(12) United States Patent
Sage-Passant

(10) Patent No.: US 8,844,848 B2
(45) Date of Patent: Sep. 30, 2014

(54) WASTE DISPOSAL APPARATUS, FLUID AND METHOD

(76) Inventor: Peter Sage-Passant, Milton Keynes (GB)

( * ) Notice: Subject to any disclaimer, the term of this patent is extended or adjusted under 35 U.S.C. 154(b) by 0 days.

(21) Appl. No.: 13/806,548

(22) PCT Filed: Jan. 25, 2011

(86) PCT No.: PCT/GB2011/000090
§ 371 (c)(1),
(2), (4) Date: Mar. 18, 2013

(87) PCT Pub. No.: WO2011/161395
PCT Pub. Date: Dec. 29, 2011

(65) Prior Publication Data
US 2013/0171713 A1  Jul. 4, 2013

(30) Foreign Application Priority Data

Jun. 22, 2010  (GB) .................................. 1010488.3

(51) Int. Cl.
| | | |
|---|---|---|
| B02C 19/00 | (2006.01) |
| B01F 7/04 | (2006.01) |
| B01F 7/00 | (2006.01) |
| C12M 1/06 | (2006.01) |
| C05F 17/00 | (2006.01) |
| B09B 3/00 | (2006.01) |
| C05G 3/00 | (2006.01) |

(52) U.S. Cl.
CPC .................. *C12M 27/02* (2013.01); *B01F 7/04* (2013.01); *B01F 7/00208* (2013.01); *C05F 17/0036* (2013.01); *B09B 3/00* (2013.01); *C05G 3/0023* (2013.01)

USPC .................. 241/36; 241/38; 241/57; 241/65; 241/100; 241/199.12; 241/101.3

(58) Field of Classification Search
USPC ........... 241/33, 57, 36, 199.12, 101.3, 38, 65, 241/100; 422/309, 287
See application file for complete search history.

(56) References Cited

U.S. PATENT DOCUMENTS

| 5,866,409 A | 2/1999 | Nibu | |
| 2009/0130256 A1* | 5/2009 | Uphoff ............................ | 426/15 |

FOREIGN PATENT DOCUMENTS

| DE | 195 30 471 | 8/1995 |
| EP | 0 611 742 | 8/1994 |
| GB | 2 286 825 | 8/1995 |
| JP | 07328594 | 12/1995 |
| JP | 09029211 | 2/1997 |
| JP | 10094774 | 4/1998 |
| KR | 10-2006-0022827 | 3/2006 |
| WO | WO 2007/075053 | 7/2007 |

OTHER PUBLICATIONS

British Search Report dated Oct. 21, 2010 for Application No. GB1010488.3.

(Continued)

*Primary Examiner* — Mark Rosenbaum
(74) *Attorney, Agent, or Firm* — Fay Sharpe LLP

(57) ABSTRACT

A waste disposal apparatus, for disposing of waste materials using aerobic decomposition, includes a decomposition chamber having a waste inlet for receiving waste materials, and a closure member for closing the inlet and sealing the decomposition chamber. The apparatus includes a stirrer for stirring waste materials in the chamber, and a waste outlet for discharging waste materials from the chamber after aerobic decomposition thereof.

22 Claims, 6 Drawing Sheets

(56) References Cited

OTHER PUBLICATIONS

International Search Report mailed Feb. 26, 2013 for International Application No. PCT/GB2011/000090.
Written Opinion mailed Feb. 26, 2013 for International Application No. PCT/GB2011/000090.

* cited by examiner

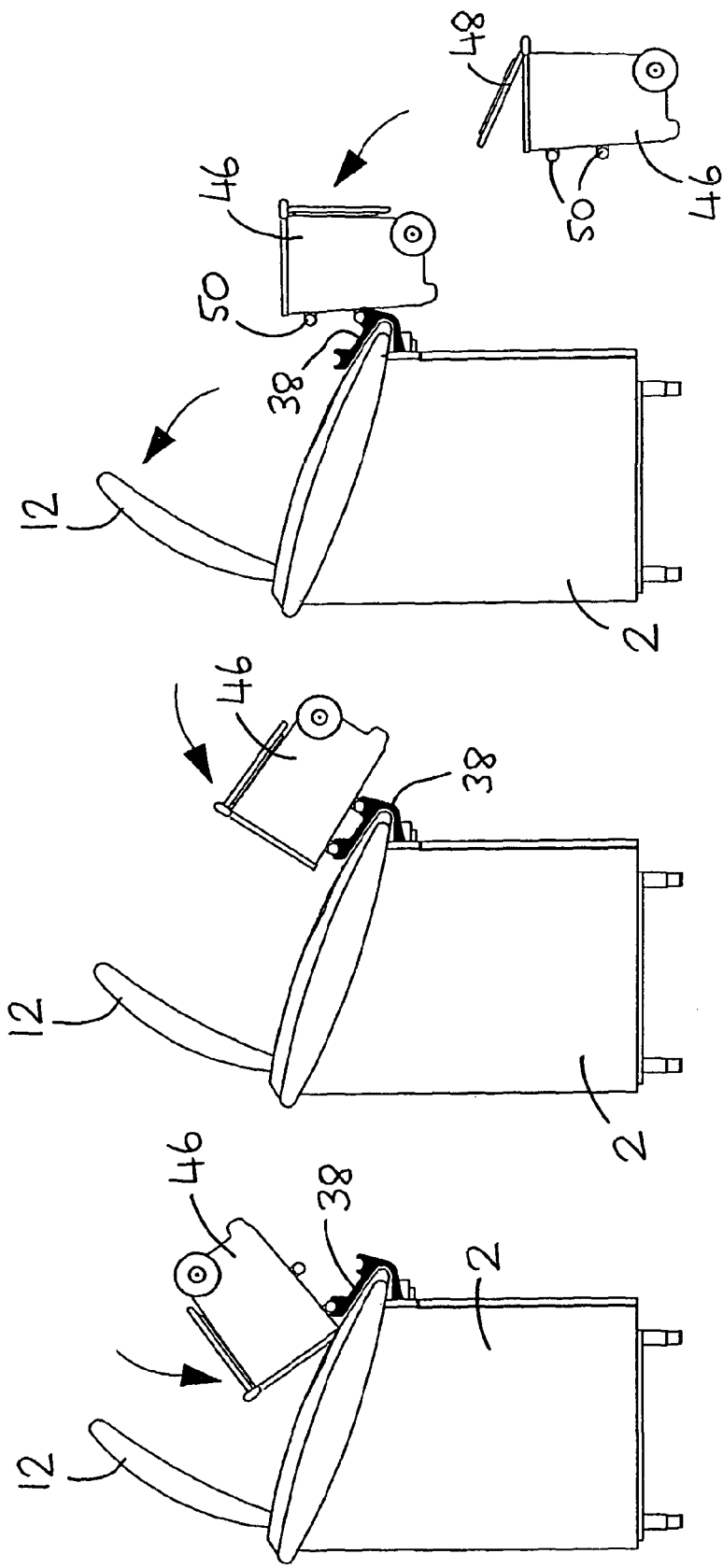

WASTE DISPOSAL APPARATUS, FLUID AND METHOD

The present invention relates to a waste disposal apparatus and in particular but not exclusively to a waste disposal apparatus for disposing of unwanted food waste using aerobic decomposition. The invention also relates to a working fluid for aerobic decomposition and a method of disposing of waste materials using aerobic decomposition.

Aerobic decomposition is a well-known method for disposing of unwanted food waste. It is useful in that it diverts food waste from landfill, which is generally agreed to be expensive, environmentally unfriendly and unsustainable.

The present invention allows for the anaerobic decomposition of food waste at the point of production, using microorganisms.

Machines exist that allow aerobic decomposition using microorganisms at the point of food waste production. However, there are a number of disadvantages associated with these existing machines.

Existing machines rely on weight-sensing load cells or visual indicators to warn the operator when the machine is full and unable to accept any more food waste. The difficulty with these designs is that there is nothing to physically prevent the operators from continuing to load food waste after the overload sensors have been actuated. This can lead to blockage, which can often result in the machine having to be manually unloaded, which is a time-consuming, unpleasant and expensive operation.

Existing machines rely on having the waste degrading microorganisms 'topped up' every few months by a service engineer. In addition, separate deodoriser fluid is often used to mask any odours released when the loading hatch is opened. This is expensive and requires the machine to be taken out of service while the microorganisms are topped up. In addition to the above, a grease trap or other means of removing the fats, oils and greases that are released into the waste stream usually has to be incorporated into the drainage line running from the machine.

Successful aerobic decomposition requires a combination of conditions to exist inside the food waste tank, including a steady temperature at around 43° C. Existing machines have food waste chambers manufactured from stainless steel, which is expensive, heavy, and has poor thermal insulation properties.

Existing machines can only be installed in well-ventilated areas because there is often an escape of vapour when the machine lid is opened.

Existing machines can be difficult to load as the operator has to lift different sized food waste bins up to the loading hatch, and then rotate the bins through 180° in order to empty them. This can result in spills which can create health and safety issues.

Existing machines use a lot of water during processing, which runs away to drain. This is expensive and environmentally unfriendly.

Existing machines are heavy, cumbersome and require permanent installation connections.

It is an object of the present invention to provide a waste disposal apparatus that mitigates one or more of the disadvantages described above.

According to one aspect of the present invention there is provided a waste disposal apparatus for disposing of waste materials using aerobic decomposition, the apparatus including a decomposition chamber having a waste inlet for receiving waste materials, a closure member for closing the inlet and sealing the decomposition chamber, a stirrer for stirring waste materials in the chamber, and a waste outlet for discharging waste materials from the chamber after aerobic decomposition thereof.

The apparatus can be used for the disposal of biodegradable waste materials, for example food waste. This allows the waste materials to be disposed of easily, quickly and hygienically and avoids the environmental and economic disadvantages associated with disposing of those waste materials in landfill sites.

Advantageously, the waste disposal apparatus includes a locking device for locking the closure member in a closed condition, a load sensing device for sensing the quantity of waste materials in the decomposition chamber and a control system that is operably connected to the load sensing device and the locking device, the control system being constructed and arranged to lock the closure member in the closed condition in response to sensing a fully loaded condition.

By locking the lid when the decomposition chamber is fully loaded, the risk of overloading and potential blocking of the chamber can be reduced or avoided. This helps to avoid the need for manually clearing a blockage.

The load sensing device may be constructed and arranged to sense the load on the stirrer during stirring. Advantageously, the stirrer includes a electric stirrer motor and the load sensing device is constructed and arranged to sense the electrical load on the stirrer motor during stirring.

Preferably, the control system is operably connected to the stirrer motor and is constructed and arranged to sense a blocked condition in which stirring of the waste material is substantially prevented, and to apply a de-blocking operational control signal to the stirrer motor in response to sensing a blocked condition. This control signal may for example cause rotation of the stirrer to reverse one or more times in order to clear the blockage.

Advantageously, the control system is constructed and arranged to activate the alarm device and/or deactivate the stirrer motor in response to sensing a sustained blocked condition. This allows the blockage to be cleared manually.

The control system is preferably constructed and arranged to release the locking device when the quantity of waste materials in the chamber falls below a second predetermined value. This second predetermined value may be a percentage of the full capacity, for example about 80% of the full capacity.

Advantageously, the waste disposal apparatus includes a dosing system for automatically dosing waste material in the decomposition chamber with a working fluid. This ensures that the working fluid is applied effectively at the correct times, and that the quantity of working fluid is controlled to avoid wastage.

Preferably, the dosing system includes a bag-in-box type supply of working fluid, in which the working fluid is contained within a flexible polymeric bag within a rigid box-like container made, for example, of cardboard. This is a very convenient way to store the working fluid and it allows the supply of working fluid to be replenished easily and quickly. Degradation of the working fluid while in storage is also reduced, since the bag of the bag-in-box container is hermetically sealed.

The dosing system preferably includes a diaphragm pump for delivering working fluid to the decomposition chamber. This allows the quantity of working fluid added to the decomposition chamber to be accurately controlled.

Advantageously, the dosing system is constructed and arranged to deliver a predetermined quantity of working fluid to the decomposition chamber each time the closure member is opened.

Advantageously, the working fluid includes a blend of bacteria, free enzymes and plant extracts. More specifically, the working fluid preferably includes a blend of the following substances, by weight: preservative 1-10%, surfactant 1-10%, enzyme 0.1-1.0%, glycol 0.1-1.0%, plant extract 0.1-1.0%, fragrance 0.1-1.0%, thickener 0.1-1.0%, bacteria 0.01-1.0%.

Advantageously, the decomposition chamber and optionally the closure member are made substantially or wholly of a polymeric material, optionally polyethylene. This improves the thermal insulation of the decomposition chamber, thus reducing or eliminating the need for external heating (some heat being generated by decomposition of the waste materials). If heating is required, this can be provided using a low power heating unit, thus reducing the energy demands of the apparatus.

The use of polymeric materials considerably reduces the weight and possibly also the size of the apparatus. It is therefore possible to design the apparatus as a mobile unit and it relatively easy to relocate the apparatus when required. The moulded components are also less likely to leak than traditional welded metal components, and they are easy to clean and maintain.

The decomposition chamber and optionally the closure member are preferably rotationally moulded components, this manufacturing process being particularly suitable for large components of this type as it allows large wall thicknesses to be formed, which increase the level of thermal insulation. The use of moulded polymeric components is also very cost effective as compared for example to stainless steel components.

The waste disposal apparatus may include a heater for heating the decomposition chamber. The heater is preferably thermostatically controlled and it may for example consist of a low power heat mat that attached to the base of the decomposition chamber.

Advantageously, the waste disposal apparatus includes a gas duct having an inlet connected to the decomposition chamber and an exterior outlet, an extractor fan for drawing gas through the duct and a filter for filtering gas drawn through the duct, the fan being constructed and arranged to operate when the closure member is in an open condition, thereby extracting gas from the decomposition chamber. This prevents odorous gases and vapours from escaping into the atmosphere when the lid is opened.

Advantageously, the waste disposal apparatus includes a bracket mounted adjacent the waste inlet for supporting a complementary waste container, the bracket being constructed and arranged to enable a waste container to be supported and pivoted about the bracket in order to tip waste materials from the waste container into the decomposition chamber. This reduces the effort needed to tip waste materials into the decomposition chamber and reduces the risk of spilling the waste materials.

The bracket may include a load sensing device for sensing the weight of the waste materials in the supported bin, and optionally a data logging device for logging data including the weight of the waste materials. This allows a log to be kept of the amount of materials disposed of in the waste disposal apparatus.

The waste disposal apparatus may include one or more complementary waste containers adapted to be supported by the bracket. The or each complementary waste container preferably includes a lid for sealing the container.

Advantageously, the waste disposal apparatus includes a water recycling system for extracting water from waste materials in the waste outlet and returning the extracted water to the decomposition chamber. This reduces both water usage and the amount of treated waste materials discharged into the drain. Preferably, the waste disposal apparatus includes a water duct for delivering water to the decomposition chamber and a valve for controlling the flow of water through the duct.

According to another aspect of the invention there is provided a working fluid for the aerobic decomposition of waste materials, preferably using a waste disposal apparatus according to any one of the preceding statements of invention, wherein the working fluid includes a blend of bacteria, free enzymes and plant extracts.

The working fluid preferably includes a blend of the following substances, by weight: preservative 1-10%, surfactant 1-10%, enzyme 0.1-1.0%, glycol 0.1-1.0%, plant extract 0.1-1.0%, fragrance 0.1-1.0%, thickener 0.1-1.0%, bacteria 0.01-1.0%.

Advantageously, the working fluid is contained in a bag-in-box type container.

According to another aspect of the invention there is provided a method of disposing of waste materials by aerobic decomposition, in which the waste materials are placed in a decomposition chamber, a working fluid that includes a blend of bacteria, free enzymes and plant extracts is applied to the waste materials, the waste materials are stirred to encourage aerobic decomposition thereof, and decomposed waste materials are discharged from the chamber.

Advantageously, the working fluid includes a blend of the following substances, by weight: preservative 1-10%, surfactant 1-10%, enzyme 0.1-1.0%, glycol 0.1-1.0%, plant extract 0.1-1.0%, fragrance 0.1-1.0%, thickener 0.1-1.0%, bacteria 0.01-1.0%.

The waste materials may for example be waste food products.

Advantageously, the method is implemented using an apparatus according to any one of the preceding statements of invention.

An embodiment of the invention will now be described by way of example with reference to the accompanying drawings, in which:

FIG. 5 is a side view of a food waste bin;

FIGS. 6, 7 and 8 are side views showing waste food being transferred from a food waste bin into the waste disposal machine.

Figure 1:
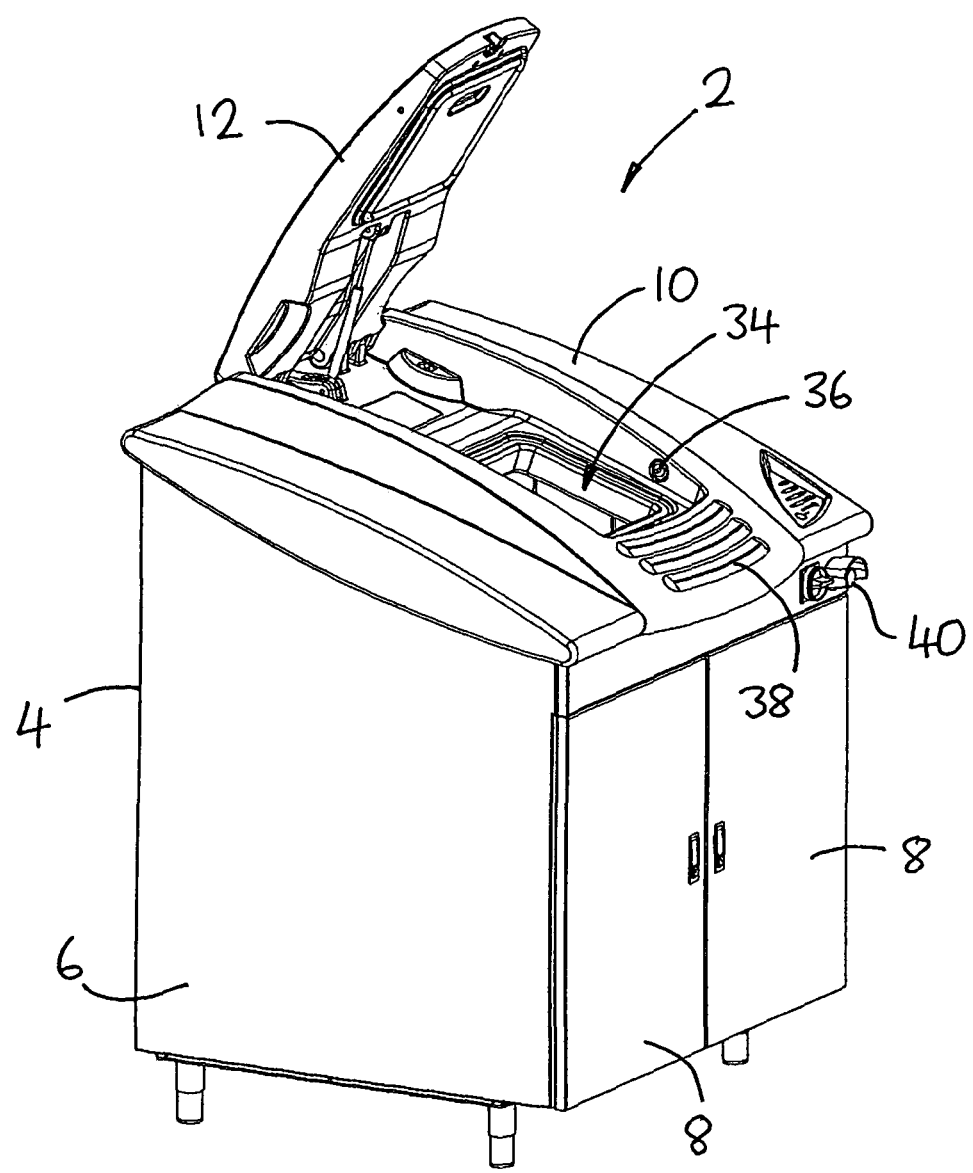
FIG. 1 is an isometric view showing the left and front sides of a waste disposal machine with an open lid.

As shown in FIGS. 1-4, the waste disposal apparatus 2 includes a cabinet 4 with two side panels 6, a rear panel 7 and two doors 8 forming the front part of the cabinet. The top side of the cabinet is closed by an inclined top cover 10 having a hinged lid 12.

Within the cabinet there is mounted a decomposition chamber 14 having a four-sided upper part 14*a* and a substantially semi-cylindrical lower part 14*b*. This decomposition chamber 14 is preferably made from a polymeric material, for example polyethylene, preferably by rotational moulding. A drain outlet (not shown) is provided in the lower part of the chamber.

Located adjacent the base of the decomposition chamber 14 is a perforated semi-cylindrical draining wall 16. The perforations in this wall are designed to allow water and other liquids to pass through the wall into the drain outlet, while retaining bulky waste materials in the chamber.

A stirring device 18 is located within the decomposition chamber 14. The stirring device includes a number of paddles 20 attached by arms 22 to a horizontal shaft 24. The shaft is mounted for rotation in bearings 26 on opposite sides of the chamber 14. One end of the shaft 24 extends through the side of the chamber and is attached to a pulley wheel 28. Rotation of the stirrer device is driven by an electric motor 30 in the lower part of the cabinet 4 via a drive belt 32.

Figure 2:
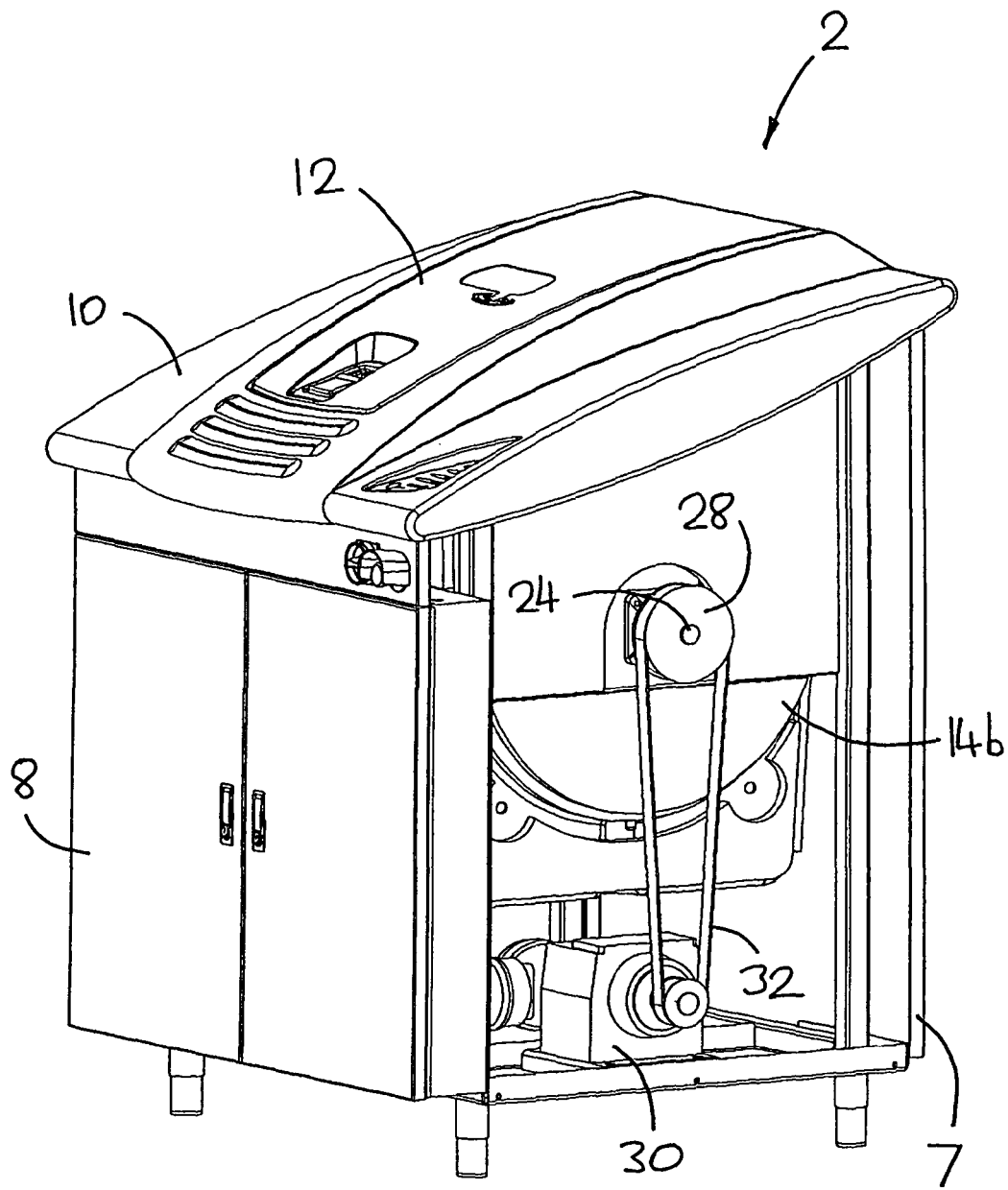
FIG. 2 is an isometric view showing the right and front sides of the waste disposal machine with a right side panel removed.
Figure 3:
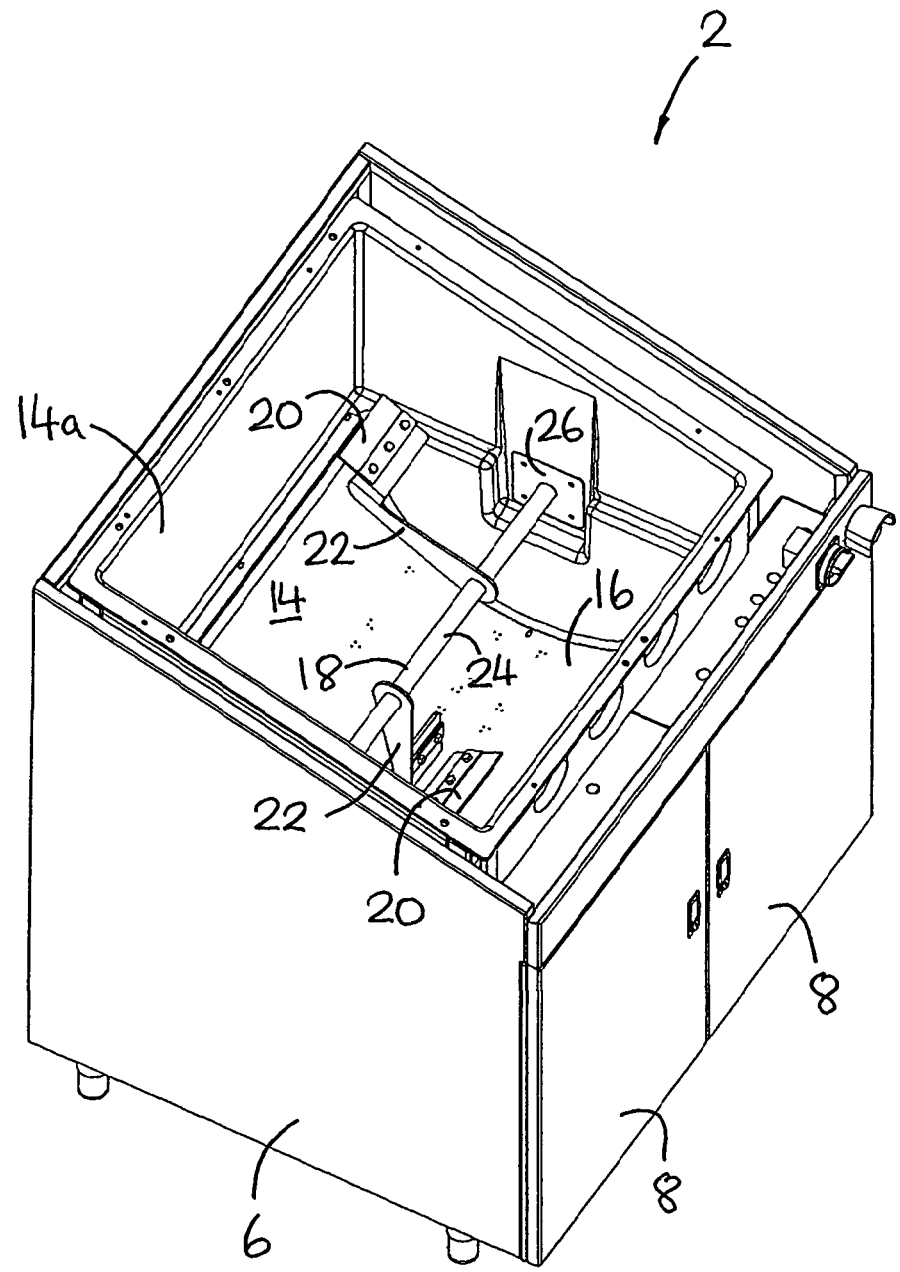
FIG. 3 is an isometric view of the waste disposal machine from above, with the top removed.

The top plate 10 includes a waste inlet 34 through which waste materials can be loaded into the decomposition chamber 14. The hinged lid 12 serves as a closure member that may be opened as shown in FIG. 1 to allow access to the waste inlet 34, or closed as shown in FIG. 2 to seal the decomposition chamber 14. The lid 12 and the top plate 10 are preferably made from a polymeric material, for example polyethylene, preferably by rotational moulding.

Figure 4:
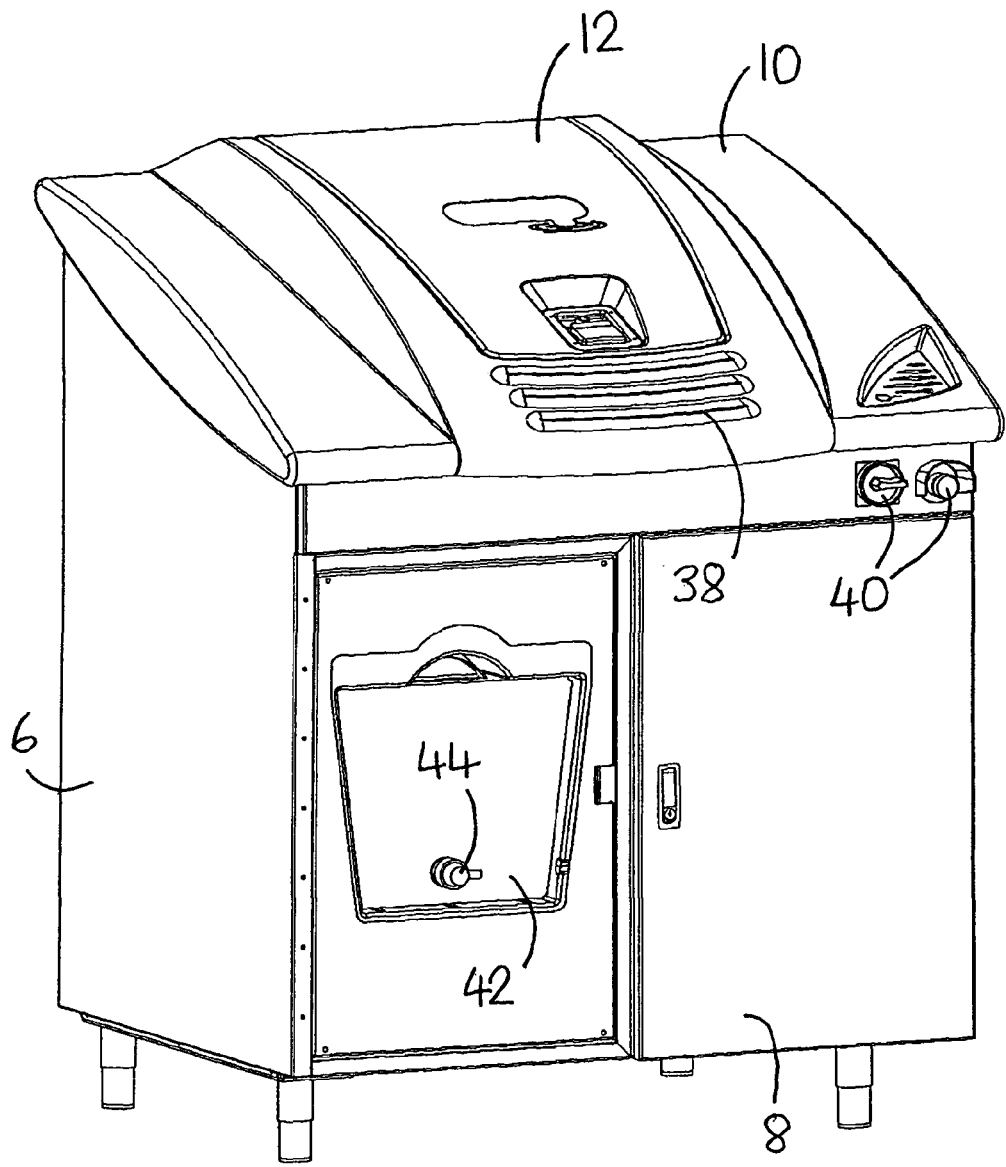
FIG. 4 is an isometric view of the waste disposal machine from the front with a door removed.

Mounted within the top plate 10 adjacent the waste inlet is a locking device 36, for example an electrically actuated latching bolt, for locking the lid 12 in a closed condition. The top plate also includes one or more brackets 38 for supporting a waste container, as will be described in greater detail below. Controls 40 for controlling operation of the waste disposal apparatus are provided on the front part of the cabinet above the doors 8. Concealed within the cabinet 4 behind one of the doors 8 is a compartment for receiving a container of working fluid 42, as shown in FIG. 4. The container 42 is preferably a bag-in-box type, having a sealed bag of fluid supported by a surrounding box or carton and having a tap or valve 44 through which working fluid can be drawn from the bag.

The working fluid includes a blend of bacteria, free enzymes and plant extracts, which are effective to promote aerobic decomposition of the waste materials including food waste, oils and greases, and which help to eliminate odours. The working fluid preferably includes a blend of the following substances, by weight: preservative 1-10%, surfactant 1-10%, enzyme 0.1-1.0%, glycol 0.1-1.0%, plant extract 0.1-1.0%, fragrance 0.1-1.0%, thickener 0.1-1.0%, bacteria 0.01-1.0%.

FIGS. 5 to 8 show how waste material can be easily transferred into the waste disposal apparatus 2 from a waste container 46. The waste container 46 consists of a substantially conventional wheeled bin 47 with a water-tight lid 48. Integrally moulded pivot points 50 are provided on one face of the container, which are designed to engage with the support bracket 38 on the top plate 10 of the waste disposal apparatus 2. In the example shown in the drawings, the waste container has two pivot points 50, which support the bin in upper and lower locations. It will be understood however that more or fewer pivot points could alternatively be provided.

In order to empty the waste container 46, it is lifted to the position shown in FIG. 6 so that the lower pivot point 50 is hooked onto the support bracket 38. It is then tipped forwards through the position shown in FIG. 7 in which both pivot points engage the bracket 38 to the inverted position shown in FIG. 8, where it is supported only by the upper pivot point. After the contents of the container have been tipped into the waste disposal apparatus, the waste container can be lowered and lifted down from the apparatus by reversing these steps. The support bracket 38 thus serves to support the container as the waste materials are tipped into the waste disposal apparatus, and ensures that the container is correctly aligned with the waste inlet to avoid spilling the waste materials.

Figure 9:
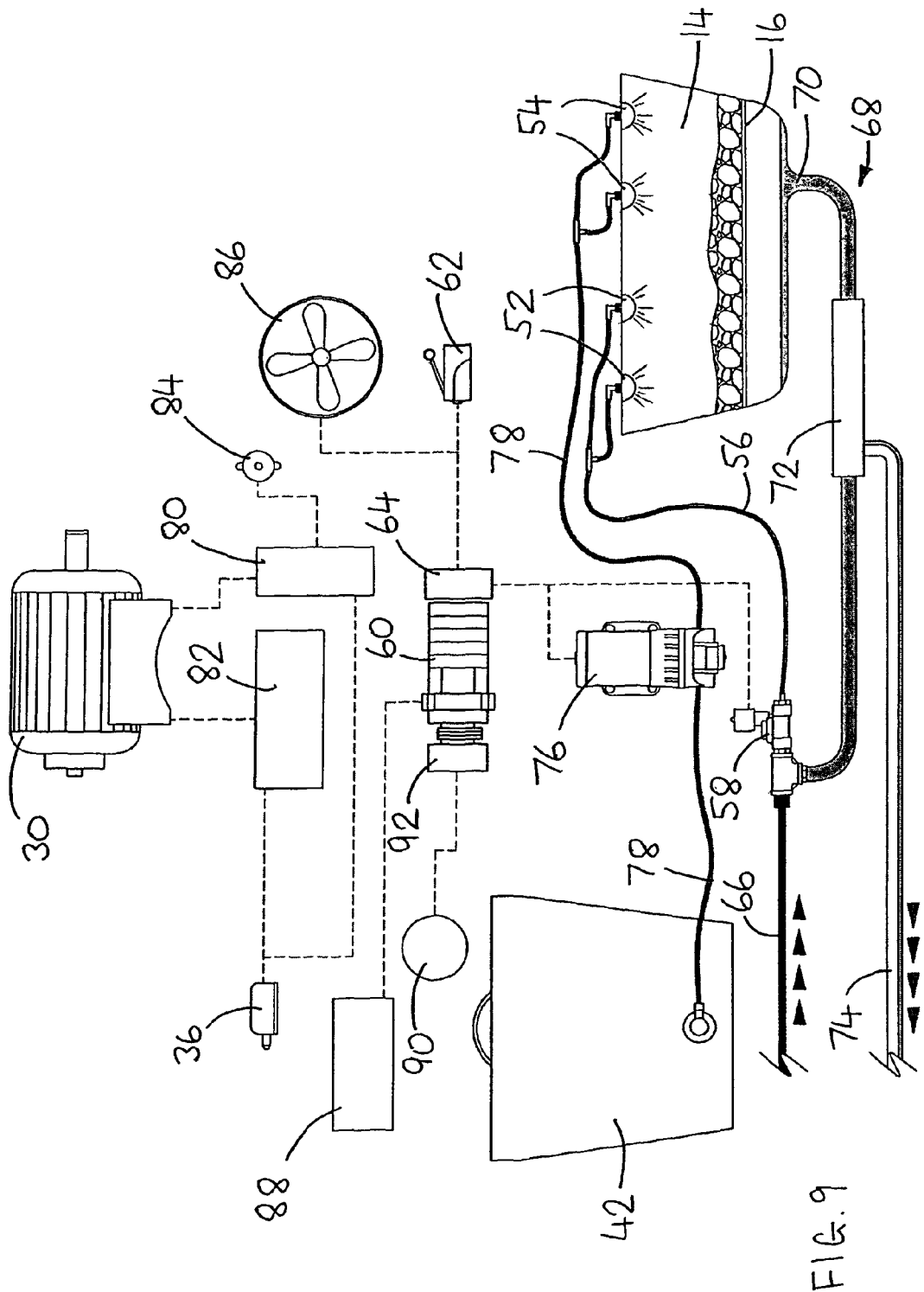
FIG. 9 is a schematic diagram showing the control system of the waste disposal machine.

The operational parts and the control system of the waste disposal apparatus are shown schematically in FIG. 9.

A plurality of spray nozzles 52,54 are located within the decomposition chamber 14. Some of these nozzles 52 are designed to spray waste materials within the chamber 14 with water, which is supplied to the nozzles 52 through water supply lines 56. The flow of water to the nozzles 52 is controlled by a solenoid valve 58, which is activated by a central control unit 60. The central control unit 60 is linked to a lid switch 62 that senses when the lid 12 is closed, and only activates the valve 58 to supply water to the decomposition chamber 14 when the lid is closed. The central control unit 60 is also connected to a timer 64 that measure the time for which the valve is open is order to control the amount of water supplied to the chamber.

Water can be supplied to the chamber either from an external water supply 66 or from a waste water recycling system 68. The waste water recycling system 68 is connected to the drain outlet 70 of the decomposition chamber 14 and includes a separator 72 that separates some of the water from the decomposed waste materials flowing from the chamber 14, the remaining portion of the waste materials flowing through an outlet pipe 74 to a drain.

The other nozzles 54 are designed to spray waste materials in the chamber 14 with a working fluid that includes a blend of bacteria, free enzymes and plant extracts. This working fluid is drawn from the fluid container 42 and supplied to the nozzles 54 by a diaphragm pump 76 via a fluid supply line 78. The pump 76 is connected to the central control unit 60, which controls its operation. The pump 76 is activated only when the lid 12 is opened and then only for a predetermined period of time determined by the timer 64, in order to control the amount of fluid supplied to the decomposition chamber 14.

The central control unit also controls operation of the motor 30 that drives the stirrer 18, and activates the stirrer only when the lid 12 is closed, as sensed by the lid switch 62. Electrical power is supplied to the motor 30 via an electrical inverter 80 and the load on the motor 30 as it drives the stirrer 18 is detected by a current sensing relay 82. The load on the motor depends on the amount of waste materials in the decomposition chamber 14, and when the chamber is loaded to its maximum capacity the relay 82 activates the latching bolt 36 to lock the lid 12 closed. The lid remains locked until some of the waste materials in the chamber have been digested and the load on the motor has fallen. The latching bolt 36 is then released, allowing the lid to be opened so that more waste materials can be loaded into the chamber.

Overloading of the chamber 14 that completely or substantially prevents rotation of the stirrer 18 can be detected by the inverter 80. When an overload condition is sensed, the central control unit 60 first attempts to release the blockage by reversing the rotation direction of the stirrer one or more times. If a sustained blocked condition is sensed that cannot be freed by reversing the stirrer, the control unit 60 shuts down the motor 30, releases the latching bolt 36 and generates an alarm signal via a sounder 84 so that the blockage can be cleared manually.

The central control unit 60 is operably connected to an extractor fan 86, which is connected via a duct (not shown) to the decomposition chamber 14 and is arranged to extract air from the chamber and discharge it through a carbon filter (not shown). Operation of the fan 86 is controlled by the lid switch 62, so that the fan is activated whenever the lid 12 is opened. This creates a partial vacuum in the decomposition chamber 14, causing ambient air to flow into the chamber through the waste inlet 34 and preventing odorous gases and vapours from escaping into the atmosphere.

The central control unit 60 is also operably connected to a thermostatically controlled heater 88 for heating the waste materials in the decomposition chamber 14 to an ideal temperature for aerobic decomposition (typically about 43 C). The heater 88 may for example consist of a low energy heater mat that is mounted against a wall or the base of the decomposition chamber 14.

The support bracket 38 is preferably connected to a load cell 90 that senses the weight of a waste container 46 supported by the bracket. As the weight of an empty container is known, this allows it to calculate the weight of waste materials loaded into the waste disposal apparatus to be calculated. This information and optionally other data, for example time and date, can then be logged by a data logger device 92 connected to the load cell 90.

In use, waste material, for example food waste, is tipped into the decomposition chamber 14 from a waste container 46. The weight of this waste material is measured by the load cell 90 and the data is logged by the data logger 92. The lid 12 is then closed. Closing of the lid 12 is sensed by the lid switch 62, whereupon the waste material in the chamber 14 is sprayed with water and working fluid through the nozzles 52,54. The motor 30 is activated to operate the stirrer 18 and if necessary the heater 88 is turned on to heat the waste materials to the ideal decomposition temperature.

If the lid 12 is opened, the motor 30 is shut down to deactivate the stirrer 18 and the extractor fan 86 is turned on to prevent odours escaping into the atmosphere. The weight of waste materials added to the chamber is sensed and logged by the load cell 90 and the data logger 92. After the waste materials have been added, the lid 12 is closed whereupon the motor 30 is reactivated and the fan 86 is deactivated. The waste material is again sprayed with water and working fluid through the nozzles 52,54.

The amount of waste material in the chamber is sensed by the current sensing relay 82. When the chamber is full, the relay fires the latching bolt 36 to lock the lid and prevent further materials being added to the chamber. As the waste is digested, it falls through the perforated wall 16 into the base of the decomposition chamber 14 from where it flows through the drain outlet 70 into a drainage system. If required, some water can be extracted from the waste fluids by the separator 72 and recycled into the chamber through the water nozzles 52. When the load in the chamber has fallen below a predetermined level, which is preferably about 80% of the maximum capacity of the chamber, the latching bolt is released so that additional waste material can be added to the chamber. If an overload situation is detected, this is resolved by the procedures described above.

The invention claimed is:

1. A waste disposal apparatus for disposing of waste materials using aerobic decomposition, the apparatus including a decomposition chamber comprising a waste inlet for receiving waste materials, a closure member for closing the inlet and sealing the decomposition chamber, a stirrer for stirring waste materials in the chamber, and a waste outlet for discharging waste materials from the chamber after aerobic decomposition thereof; said waste disposal apparatus further including a locking device for locking the closure member in a closed condition, a load sensing device for sensing the quantity of waste materials in the decomposition chamber and a control system that is operably connected to the load sensing device and the locking device, the control system being constructed and arranged to lock the closure member in the closed condition in response to sensing a fully loaded condition.

2. A waste disposal apparatus according to claim 1, wherein the load sensing device is constructed and arranged to sense the load on the stirrer during stirring.

3. A waste disposal apparatus according to claim 2, wherein the stirrer includes an electric stirrer motor and the load sensing device is constructed and arranged to sense the electrical load on the stirrer motor during stirring.

4. A waste disposal apparatus according to claim 3, in which the control system is operably connected to the stirrer motor and is constructed and arranged to sense a blocked condition in which stirring of the waste material is substantially prevented, and to apply a de-blocking operational control signal to the stirrer motor in response to sensing a blocked condition.

5. A waste disposal apparatus according to claim 4, in which the control system is constructed and arranged to activate an alarm device and/or deactivate the stirrer motor in response to sensing a sustained blocked condition.

6. A waste disposal apparatus according to claim 1, in which the control system is constructed and arranged to release the locking device when the quantity of waste materials in the chamber falls below a second predetermined value.

7. A waste disposal apparatus according to claim 1, further including a dosing system for automatically dosing waste material in the decomposition chamber with a working fluid.

8. A waste disposal apparatus according to claim 7, in which the dosing system includes a bag-in-box type supply of working fluid.

9. A waste disposal apparatus according to claim 7, in which the dosing system includes a diaphragm pump for delivering working fluid to the decomposition chamber.

10. A waste disposal apparatus according to claim 7, in which the dosing system is constructed and arranged to deliver a predetermined quantity of working fluid to the decomposition chamber each time the closure member is opened.

11. A waste disposal apparatus according to claim 7, in which the working fluid includes a blend of bacteria, free enzymes and plant extracts.

12. A waste disposal apparatus according to claim 11, in which the working fluid includes a blend of the following substances, by weight: preservative 1-10%, surfactant 1-10%, enzyme 0.1-1.0%, glycol 0.1-1.0%, plant extract 0.1-1.0%, fragrance 0.1-1.0%, thickener 0.1-1.0%, bacteria 0.01-1.0%.

13. A waste disposal apparatus according to claim 1, in which the decomposition chamber and optionally the closure member are made substantially or wholly of a polymeric material, optionally polyethylene.

14. A waste disposal apparatus according to claim 13, in which the decomposition chamber and optionally the closure member are rotationally moulded components.

15. A waste disposal apparatus according to claim 13, further including a heater for heating the decomposition chamber, said heater optionally comprising a heat mat attached to the decomposition chamber.

16. A waste disposal apparatus according to claim 1, further including a gas duct having an inlet connected to the decomposition chamber and an exterior outlet, an extractor fan for drawing gas through the duct and a filter for filtering gas drawn through the duct, the fan being constructed and arranged to operate when the closure member is in an open condition, thereby extracting gas from the decomposition chamber.

17. A waste disposal apparatus according to claim 1, further including a water recycling system for extracting water from waste materials in the waste outlet and returning the extracted water to the decomposition chamber.

18. A waste disposal apparatus according to claim 1, further including a water duct for delivering water to the decomposition chamber and a valve for controlling the flow of water through the duct.

19. A waste disposal apparatus for disposing of waste materials using aerobic decomposition, the apparatus including a decomposition chamber comprising a waste inlet for receiving waste materials, a closure member for closing the inlet and sealing the decomposition chamber, a stirrer for stirring waste materials in the chamber, and a waste outlet for discharging waste materials from the chamber after aerobic decomposition thereof; said waste disposal apparatus further including a bracket mounted adjacent the waste inlet for supporting a complementary waste container, the bracket being constructed and arranged to enable a waste container to be supported and pivoted about the bracket in order to tip waste materials from the waste container into the decomposition chamber.

20. A waste disposal apparatus according to claim 19, in which the bracket includes a load sensing device for sensing the weight of the waste materials in the supported bin, and optionally a data logging device for logging data including the weight of the waste materials.

21. A waste disposal apparatus according to claim 19, further including one or more complementary waste containers adapted to be supported by the bracket.

22. A waste disposal apparatus according to claim 21, in which the or each complementary waste container includes a lid for sealing the container.

\* \* \* \* \*